United States Patent
Bob et al.

(10) Patent No.: US 12,075,977 B2
(45) Date of Patent: Sep. 3, 2024

(54) ENDOSCOPE DEFLECTION USING A DISTAL FOLDING MECHANISM

(71) Applicant: Konstantin Bob, Weinheim (DE)

(72) Inventors: Konstantin Bob, Weinheim (DE); Andreas Gründl, Starnberg (DE)

(73) Assignee: Konstantin Bob, Weinheim (DE)

( * ) Notice: Subject to any disclaimer, the term of this patent is extended or adjusted under 35 U.S.C. 154(b) by 622 days.

(21) Appl. No.: 17/052,453

(22) PCT Filed: May 3, 2019

(86) PCT No.: PCT/EP2019/061420
§ 371 (c)(1),
(2) Date: Nov. 2, 2020

(87) PCT Pub. No.: WO2019/211456
PCT Pub. Date: Nov. 7, 2019

(65) Prior Publication Data
US 2021/0137354 A1  May 13, 2021

(30) Foreign Application Priority Data
May 3, 2018  (DE) .................. 10 2018 110 620.3

(51) Int. Cl.
*A61B 1/005*  (2006.01)
*A61B 1/00*  (2006.01)
(Continued)

(52) U.S. Cl.
CPC ........ *A61B 1/0056* (2013.01); *A61B 1/00098* (2013.01); *A61B 1/0057* (2013.01); *A61B 1/012* (2013.01); *A61B 1/273* (2013.01)

(58) Field of Classification Search
CPC ................ A61B 1/00098; A61B 1/012; A61B 1/0056–0057
See application file for complete search history.

(56) References Cited

U.S. PATENT DOCUMENTS 4,245,624 A * 1/1981 Komiya .................. A61B 1/12
  604/95.04
4,353,358 A * 10/1982 Emerson ................. A61B 1/31
  600/146
(Continued)

FOREIGN PATENT DOCUMENTS

DE        10143966 A1    3/2002
DE    102012220578 A1    5/2014
(Continued)

OTHER PUBLICATIONS

Written Opinion of the International Searching Authority received in Application No. PCT/EP2019/061420 dated Jul. 16, 2019, 12 pages.
(Continued)

*Primary Examiner* — Matthew J Kasztejna
(74) *Attorney, Agent, or Firm* — Christopher A. Rothe; Culhane PLLC (57) ABSTRACT

An endoscope with a folding mechanism for foldably or bendably holding an endoscopy head at the distal end of the endoscope, preferably an endoscope shaft, having a number of axially successive segments that are adjustable via an actuating element. The segments define at least one channel for the passage of minimally invasive surgical instruments, flushing media, supply lines and the like. The segments are in the form of wedge-shaped cylinder sections having end faces oriented relative to each other in a wedge-shaped manner. Each cylinder section receives a cylinder jacket portion having a minimum axial length and an opposite cylinder jacket portion having a maximum axial length. Two directly adjacent segments are mutually oriented such that they are axially supported on or axially abut the relevant cylinder jacket portions of maximum axial length, which (Continued)

results in hinge- or joint-contact occurring on the support or placement point.

14 Claims, 4 Drawing Sheets

(51) Int. Cl.
    *A61B 1/012*     (2006.01)
    *A61B 1/273*     (2006.01)

(56) References Cited

U.S. PATENT DOCUMENTS

| | | | |
|---|---|---|---|
| 4,653,476 A * | 3/1987 | Bonnet | A61B 1/018 |
| | | | 600/153 |
| 4,911,148 A | 3/1990 | Sosnowski et al. | |
| 5,284,128 A * | 2/1994 | Hart | A61B 17/00234 |
| | | | 600/209 |
| 6,270,453 B1 | 8/2001 | Sakai | |
| 6,482,149 B1 | 11/2002 | Torii | |
| 6,749,560 B1 * | 6/2004 | Konstorum | A61B 1/00071 |
| | | | 604/525 |
| 7,637,905 B2 * | 12/2009 | Saadat | A61B 1/0055 |
| | | | 606/1 |
| 2002/0032371 A1 | 3/2002 | Torii | |
| 2004/0138525 A1 | 7/2004 | Saadat et al. | |
| 2004/0199052 A1 * | 10/2004 | Banik | A61B 1/00071 |
| | | | 600/142 |
| 2005/0096502 A1 * | 5/2005 | Khalili | A61B 34/72 |
| | | | 600/129 |
| 2008/0051802 A1 | 2/2008 | Schostek et al. | |
| 2008/0208001 A1 | 8/2008 | Hadani | |
| 2008/0287741 A1 | 11/2008 | Ostrovsky et al. | |
| 2010/0228086 A1 | 9/2010 | Ohki et al. | |
| 2015/0238068 A1 | 8/2015 | Rose et al. | |
| 2016/0317138 A1 | 11/2016 | Kasic, II et al. | |

FOREIGN PATENT DOCUMENTS

| | | |
|---|---|---|
| DE | 102013222279 A1 | 5/2015 |
| EP | 1886620 A2 | 2/2008 |

OTHER PUBLICATIONS

International Search Report received in Application No. PCT/EP2019/061420 dated Jul. 16, 2019, 5 pages.
German Search Report received in Application No. 10 2018 110 620.3 dated Apr. 9, 2019, 18 pages.

* cited by examiner

ENDOSCOPE DEFLECTION USING A DISTAL FOLDING MECHANISM

CROSS-REFERENCE TO RELATED APPLICATIONS

This application is the United States national phase of International Application No. PCT/EP2019/061420, filed May 3, 2019, which claims the benefit of priority of German Application No. 10 2018 110 620.3, filed May 3, 2018. The contents of International Application No. PCT/EP2019/061420 and German Application No. 10 2018 110 620.3 are incorporated by reference herein.

FIELD

The present invention relates to a folding mechanism of an endoscope shaft for the bendable connection of a distal tip of the endoscope shaft with a proximal endoscope head portion as well as an endoscope head attachment for an endoscope with such a folding mechanism.

BACKGROUND

Endoscopes are medical working tools used for the visual exploration of cavities in the body of a patient. They basically have optical devices at the distal endoscope end, i.e. the endoscope end facing the body (also known as endoscope head) and optionally a work channel which, starting from a proximal (not facing the body) endoscope portion or extracorporeal endoscope handle, extends through an (adjoining) flexible/bend-proof or rigid endoscope shaft to the endoscope head and enables the extracorporeal insertion and use of medical instruments such as forceps, scissors, needles, slings, knifes and the like.

Such endoscopes can optionally be provided with additional functions, e.g. by placing a cap or sleeve on the distal endoscope end/endoscope head radially on the outside of the endoscope head, which is provided or equipped with specific functions/functional elements, whereby the endoscope can not only be used for exploration and/or as access for therapeutic applications, but the endoscope itself can also be used as a minimally invasive instrument for performing a surgical procedure. Alternatively, it is provided to integrally equip special endoscopes for very specific medical applications with such capacities, wherein such special designs are only suitable for this respective special application, however.

Various diagnostic and/or therapeutic procedures require, for example, imaging and/or, if necessary, therapeutic techniques on the biliary and/or pancreatic duct as well as on the hepatic ducts of the patient. Since the major duodenal papilla, which forms the common outlet of the biliary and pancreatic duct into the duodenum, protrudes laterally into the duodenum, conventional prograde endoscopes (facing in the longitudinal direction of the endoscope) are unsuitable for such procedures, since there is not enough pivoting space in the narrow duodenum (diameter 3 to 4 cm) to orientate their prograde optical unit and the work channel in a lateral-facing position, since a typical bending diameter of such devices is at about 12 cm.

From the prior art (e.g. US 2010/228086 A), duodenoscopes are known which are specially made for this purpose, which have a lateral (laterally facing) or retrograde (backward facing) optical unit (also called "side optics") as well as a laterally oriented work channel. At the exit of the work channel of such duodenoscopes, a so called Albarran lever is usually provided, which allows a targeted guidance/deflection of a tool guided in the work channel by pivoting. The laterally facing arrangement of the functional units on the endoscope head allows imaging and treatment in the duodenum area while optimally utilizing the available space.

However, such endoscopes with side optics are very complex and expensive to manufacture and have therefore been developed and manufactured so far as reusable devices. The curved work channel of such endoscopes as well as the complex construction with many undercuts of the Albarran lever have proven to be difficult to sterilize in practice or the sterilization process has turned out to be too material fatiguing for the sensitive devices, so that only disinfection is possible after a procedure with such a duodenoscope. As a result, a bacterial lawn (biofilm) may remain in the work channel and/or the auxiliary channel of the endoscope after a procedure. If this biofilm then peels off during a subsequent procedure, for example when an instrument is pushed through the work channel, it can, for example, enter the biliary duct and/or the pancreas duct and cause serious inflammation or even sepsis in the patient.

Furthermore, such devices have the disadvantage that they can only be used for very few, very specific procedures in the area of the duodenum, since neither the optical unit nor the work channel can be directed in the prograde direction. Moreover, navigation in the body with laterally facing endoscopes is generally rather difficult, since looking ahead always requires bending of the "deflection portion" (actively bendable endoscope shaft-portion) directly upstream of the endoscope head by about 90°, which in turn requires more space in the lateral direction of the endoscope, which is only available in the stomach.

The distal deflection portion of the shaft of a prograde flexible endoscope (looking straight ahead) with a bendable tip usually consists of articulated ring elements which form the supporting structure of the shaft and are operated and tilted against each other via Bowden cables, often called bending control cables. In order to facilitate insertion into the cavity and to prevent the intrusion of substances, the ring elements are surrounded by a flexible sheath made of a plastic material. In particular light and image guide cables, channels for fluids or endoscopic working instruments run inside the ring elements. The bending control cables are guided along the outside or inside of the ring elements. Such flexible endoscopes are disclosed, for example, in U.S. Pat. Nos. 6,270,453 B1, 6,482,149 B1 or DE 101 43 966 B4.

The smallest radius of curvature that the flexible or articulated portion of the shaft can assume is determined by the respective construction principle. For example, an articulated portion constructed with successive ring elements, each of which is articulated to the next, allows only a relatively large bending radius, since the individual ring elements each have only a small tilt angle to the next ring element. If the articulated connection of two elements only permits tilting about one axis, it is necessary for a spatial bending possibility to arrange elements with tilting axes alternately twisted against each other, so that only every second element can be deflected in a respectively desired direction; this further increases the possible minimum bending radius. The close range next to the shaft end is therefore not visible with an optical unit arranged in the tip of the endoscope.

As described, for example, in the prior art in DE 10 2013 222 279 A1 or DE 10 2012 220 578 A1, endoscopes with a pivoting optical unit separate from the rest of the endoscope head are furthermore known, which can look both in the prograde and in the lateral direction. However, such endoscopes do not have a work channel (i.e. they are used purely diagnostically) or they have a fixed work channel in the prograde direction and are therefore not suitable for the typically intended purposes of duodenoscopes which require a laterally-oriented work channel.

In summary, it can be said that the user is not able to perform minimally invasive interventions in the duodenum both in the prograde direction as well as in the lateral/retrospective close range of the endoscope with the endoscopes known to the prior art to date.

SUMMARY

In view of the disadvantages of the prior art described above, the object of the present invention is to provide a folding mechanism for an endoscope shaft which enables monitoring and the integrated, minimally invasive surgical treatment of the close range surrounding the endoscope tip.

A folding mechanism according to the invention for foldable or bendable mounting of an endoscope head at the distal end of an endoscope with a number of axially successive segments which are actively adjustable in angle relative to each other via at least one actuating element and said segments defining at least one channel in an axial direction for the passage of minimally invasive surgical instruments, flushing media, supply lines and the like. According to the invention, the segments are designed as wedge-shaped/wedge-like cylinder sections with front sides oriented towards each other in a wedge shape, whereby each cylinder section receives a cylinder jacket portion with minimum axial length and cylinder jacket portion with maximum axial length, which is arranged in the opposite half of the cross-section of the respective segment, in particular it is substantially diametrically opposite, wherein two respective directly adjacent segments are oriented to each other in such a way that they are axially supported or rest on each other at their respective cylinder jacket portions of maximum axial length, whereby a hinge contact or joint contact is created at the support or rest site.

In other words, in the folding mechanism according to the invention, each segment forms a kind of wedge tip or a portion of minimum axial length on a portion of its jacket surface, i.e. on a radially outer portion. The segments successively arranged in the axial direction of the endoscope are arranged relative to each other in such a way that said wedge tips are each in alignment when the folding mechanism is in a straight position. An area of maximum axial extension of the individual segments is located in an area of the respective segment facing away from the wedge tip. These areas of maximum axial extension are also in alignment when the folding mechanism is in the straight position and form an articulated or tilting contact between adjacent segments.

In other words, a folding mechanism of an endoscope shaft connects a distal tip of the endoscope shaft to a proximal portion of the endoscope (shaft), providing a bending function. The folding mechanism has a number of axially successive segments which are angle adjustable with respect to each other via at least one actuating element and which define (in the inside their cross-section) at least one channel extending in the axial direction of the endoscope shaft for the passage of minimally invasive surgical instruments, flushing media, supply lines and the like. The individual segments of the folding mechanism according to the invention in their basic shape as wedge-shaped (circular) cylinder sections, which, at their ends facing away from the wedge tip and being wider in the axial direction, each adjoin on resting portions or articulated portions in an angle adjustable manner. Due to the wedge shape of the segments and the axially aligned or adjacent arrangement of the respectively adjacent, widest portions of the wedge shape, the relative center of rotation of the respectively adjacent segments can be shifted as far as possible into the edge area, whereby a comparatively large clear space can be created between the tips of the wedge shapes, and a relatively large, possible tilt angle can be achieved between the individual segments. This results in a comparatively small bending radius of the folding mechanism, so that in contrast to prograde endoscopes, which are only equipped with a conventional deflection, also the lateral close range can be processed and viewed through an endoscope with such a folding mechanism.

Preferably, the actuating element for angle adjustment between the segments can be designed as at least one traction element which, by applying traction to the wedge-shaped segment located farthest in the distal direction, contracts the wedge tips of the segments and thus causes the folding mechanism to fold/bend. Preferably, at least one channel for the at least one traction element can be formed axially through the respective segments so that it runs in an inner lumen of the segments. Preferred configurations for the traction element are, for example, cable pulls. Especially preferably, the traction element may be designed as a Bowden cable, which is at least indirectly anchored or supported on the most distal and on the most proximal segment and braces them against each other for folding/bending the folding mechanism.

Returning to the straight position can be achieved either via shear stiffness (as with a shear-stiff Bowden cable) or by the inherent elasticity of the connection of the wedge segments or also with integrated spring elements. If necessary, this return can also go slightly beyond the straight position in order to extend the field of vision and to pre-tension the tip of the endoscope when in the straight position, thus stiffening it.

According to a preferred embodiment of the invention, the traction element running in the axial direction can be arranged in the end regions of the segments facing away from the wedge tips, but can be offset radially inwards relative to the support or rest sites of the segments, so that when a tractive force is applied, it forms a lever relative to the support or rest sites of the segments contracting the wedge tips. In other words, the at least one traction element may be arranged close to the support or rest site, but viewed from the support or rest site towards the inside of the endoscope, so that the wedge-shaped segments fold towards each other when a traction force is applied to at least the distal segment and lie flat against each other in their final position. The arrangement of the traction elements on the side of the wedge-shaped segments facing away from the wedge tips (from the inner bending radius) results in a shorter lever, which increases the required forces, but has the advantage that the area of the wedge tips (of the inner bending radius) of the segments can be made thinner (lower), which means that a smaller bending radius can be achieved in the maximum folded/bent position of the folding mechanism.

According to a further configuration of the invention, the number of wedge-shaped segments as well as the angles of the respective wedge shapes of the segments can be adapted to each other in such a way that in a maximum folded position of the folding mechanism, a folding angle of at least 80°, preferably at least 90°, particularly preferably at least 110° results. In other words, the sum of the angles of the wedge tips can be more than 80°, so that in a maximum angled position of the folding mechanism, in which the respectively adjacent segments lie flat against each other, the distal end surface of the distal end segment is angled by 80° or more relative to the longitudinal axis of the endoscope. In particular for treatments of the major duodenal papilla, folding angles >90° are advantageous, since depending on the anatomical conditions, the papilla can only be reached retrospectively.

According to another aspect, the segments can be designed in their wedge shape such that in the maximum folded position of the folding mechanism, the inner radius of curvature of the folding mechanism is less than twice the diameter of the folding mechanism, preferably less than the single diameter of the folding mechanism. Especially preferably, the inner radius of curvature of the folding mechanism in the maximum folded position (e.g. a position angled at 90°) can be smaller than half the diameter of the folding mechanism. For the folding mechanism according to the invention, it is particularly advantageous if the distal folding of the head can be performed with a minimum swivel radius or radius of curvature in order to be able to view the close range near the shaft end even in narrow body cavities.

According to a preferred embodiment of the invention, the distal front side of the endoscope head may, in a position of the folding mechanism folded down by 90°, project less than 2 cm, preferably less than 1 cm, especially preferably less than 0.5 cm, over the lateral jacket surface of the folding mechanism in the prograde orientation. For this purpose, the folding mechanism may be configured in such a way that it (or its jacket surface) forms an inner radius of curvature of less than 1 cm, preferably less than 0.5 cm, when folded by 90°.

According to another aspect of the invention, the folding mechanism may have between 3 and 5, preferably 4, wedge-shaped segments. It has been found that a number of segments in this range is particularly good at achieving folding in a lateral direction of view with a bending radius which is as small as possible.

Preferably, the working channel can be arranged in the region of the outer radius of the bend of the folding mechanism. This has the effect that the bending radius of the working channel does not become too small/narrow, so that minimally invasive surgical instruments can still be passed through.

According to a preferred embodiment of the invention, two cable pulls may be provided in the end regions of the segments which face away from the wedge tips and between which a working channel is arranged (also in the region facing away from the wedge tips) for the passage of minimally invasive surgical instruments. Such an arrangement has proven to be particularly space-efficient.

According to a preferred embodiment, the cylinder jacket portion with maximum axial length may not be diametrically opposite the cylinder jacket portion of minimum axial length but can be offset inwards towards the core of the endoscope.

According to a further configuration of the invention, the working channel may have an oval cross-section, the longest diameter of which runs in the folding direction of the folding mechanism. In this way, a narrowing of the working channel during the bending can be counteracted and the push-through capability of minimally invasive surgical instruments is maintained even in a state of 90° or more. The oval cross section of the working channel also allows sensitive orientation of the tool, as the flexible shaft proximally connected to the rigid tool tip can be moved laterally in the oval working channel, allowing fine adjustment of the tool (analogous to the fine adjustment possible in conventional duodenoscopes with the Albarran lever).

According to another aspect of the invention, the support or rest sites between the segments may be designed as film hinges. In this way, the basic structure of the folding mechanism can be manufactured in one piece, e.g. as an injection molded part or by additive manufacturing processes. However, it is also possible to provide other common hinge arrangements or just defined rest surfaces where the separately formed segments tilt against each other. In an embodiment with separate segments, these can be held against each other, for example, by a suitable sheathing.

According to a preferred embodiment of the invention, the wedge-shaped segments may be recessed in alignment in the area of their wedge tip, so that a rib-like structure results towards the inner radius of curvature of the folding mechanism. In this way, an inner lumen of the endoscope is defined, in which spray or suction channels, cooling channels, electrical lines for supplying lighting means and imaging and the like can be guided.

A further aspect of the invention, relates to an actively deflectable portion of an endoscope shaft—also called deflection—for the bendable connection of a distal tip of the endoscope shaft with a proximal endoscope shaft portion. Said deflection comprises a plurality of axially successive segments which are angularly adjustable relative to each other via at least one actuating element and which define in the axial direction at least one channel for the passage of minimally invasive surgical instruments, flushing media, supply lines and the like. The actively deflectable portion has, according to the invention, a proximal portion which can be deflected in at least two different directions and has at its distal end region a folding mechanism, in particular manufactured integrally with the proximal portion, according to one of the aforementioned aspects. In other words, an endoscope deflection known from the prior art can be adapted in such a way that its distal limbs form a folding mechanism as described above. An endoscope with such a deflection configured in this way thus has the usual curvature functions of conventional endoscopes and, in addition, an independent folding function of the endoscope tip. For this purpose, it is advantageous if the proximal deflection portion and the folding mechanism each have separate actuation elements/control mechanisms (e.g. Bowden cables). The control mechanism of the folding mechanism can advantageously be guided through suitable channels in the proximal, actively deflectable shaft portion.

A further aspect of the invention, relates to an endoscope head of the endoscope-adaptive type in the form of a separate, additional endoscope head attachment. This attachment has a proximal folding mechanism according to one of the aspects described above, which in turn has a fastening means at its proximal end for detachable attachment to the endoscope head of a (separate) endoscope. In order to actuate the folding mechanism, its actuation device (e.g. a Bowden cable) is guided along the adapted endoscope or within the working channel of the adapted endoscope in the proximal direction towards the user.

DETAILED DESCRIPTION

Figure 1:
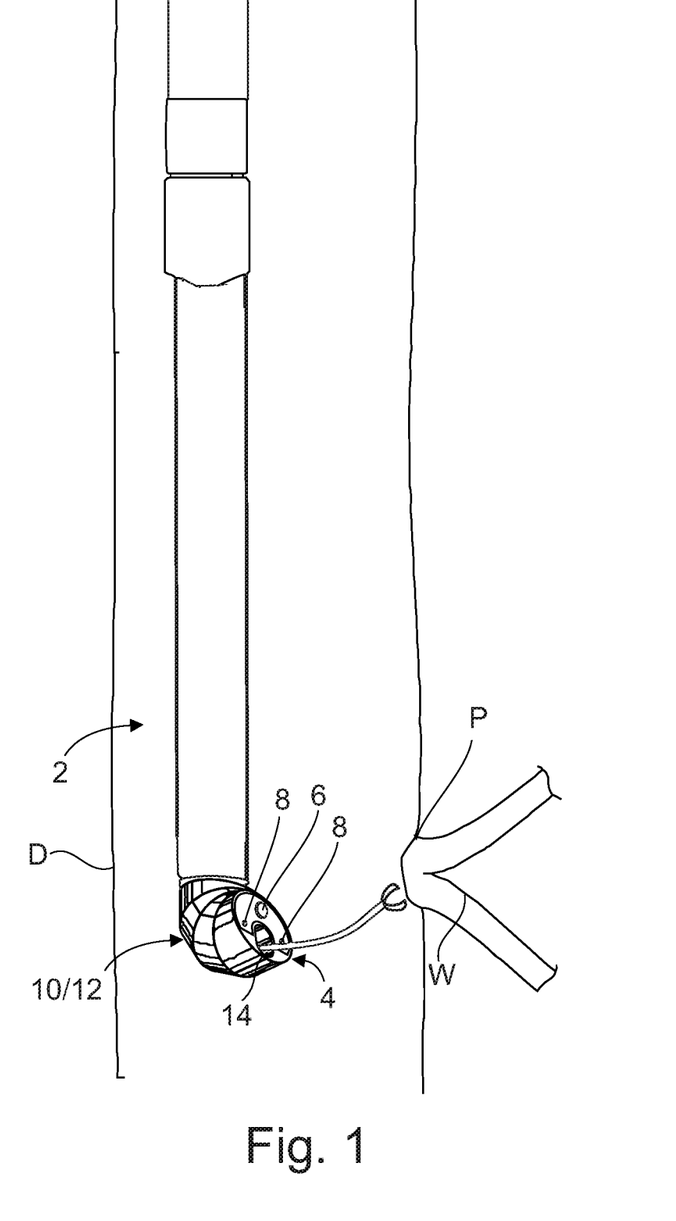
FIG. 1 is an illustration for visualizing an application area of an endoscope with a folding mechanism according to the invention.

FIG. 1 serves to explain a preferred field of application of an endoscope according to the invention or a folding mechanism according to the invention.

As can be seen from FIG. 1, the major duodenal papilla (P) is located in the rearward (dorsal) descending part (pars descendens) of the duodenum (D) and relatively difficult to access due to the tortuous geometry of this system. The space available in the region of the duodenum (D) is very limited, which means that procedures on the major duodenal papilla (P) are not possible with common prograde endoscopes, since at an appropriate angle, the endoscope tip would no longer have sufficient distance to the lumen of the duodenum (D) for proper imaging in the direction of the procedure portion.

Due to this reason, the aforementioned duodenoscopes are known from the prior art, which have a fixed sideways or retrospective optical unit as well as a correspondingly oriented working channel in order to make optimum use of the available space. However, such duodenoscopes have the disadvantage that they are fixed in their lateral/retrograde orientation of the optical unit and the working channel. On the one hand, this makes general navigation within the patient difficult and on the other hand makes such endoscopes inflexible in their possible applications. In other words, they are expensive special devices for a narrowly limited field of application.

A basic idea of the present invention is therefore to provide a folding mechanism for an endoscope, via which the endoscope head, which carries the optics and the working channel outlet of the endoscope, can be jointly pivoted by at least 90° for this purpose without requiring a large bending radius.

Figure 2:
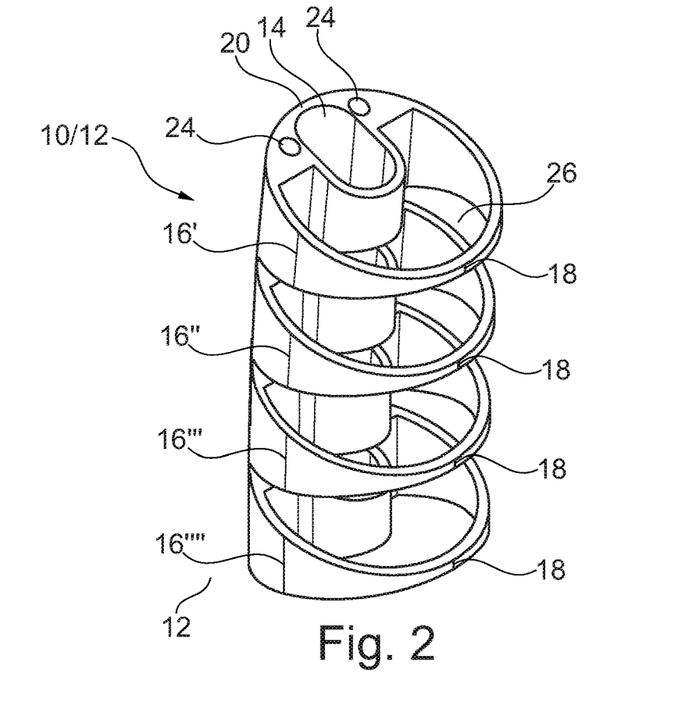
FIG. 2 is an illustration of a basic structure of a folding mechanism according to the invention in a completely upright position.

FIG. 2 shows a first exemplary embodiment of a folding mechanism 10 according to the invention in a first prograde orientation. At the distal end of the folding mechanism, an endoscope head 4 (shown in FIG. 1) is arranged in the fully assembled endoscope 2, which has different functional units such as an optical unit 6; lighting means 8 and a working channel 14. For the sake of clarity, only the most necessary functional units mentioned above are shown in FIG. 1 and in the following text; of course, an endoscope head according to the invention can also have various other functional units known from the prior art, such as e.g. cleaning nozzles for an objective of the optical unit 6, suction channels, etc.

The shown folding mechanism has a base body 12 with a number of segments 16 (16', 16", 16'" and 16") arranged in succession in the axial direction of the endoscope. The individual segments 16 basically have a wedge-like shape, i.e. their distal and proximal front faces converge at an acute angle and meet in a wedge tip 18. Accordingly, the axial extension of the individual segments 16 is greatest in the portion 20 (diametrically opposite) facing away from the wedge tip 18. In the embodiment shown, the individual segments 16 also have a circular-cylinder sectional shape in order to achieve a circular cross-section of the entire endoscope 2. As can be clearly seen in FIG. 2, the wedge tips 18 and the portions 20 facing away from them are aligned in the upright/extended position of the folding mechanism 10. As a result, the folding mechanism 10 can be bent unidirectionally.

Figure 3:
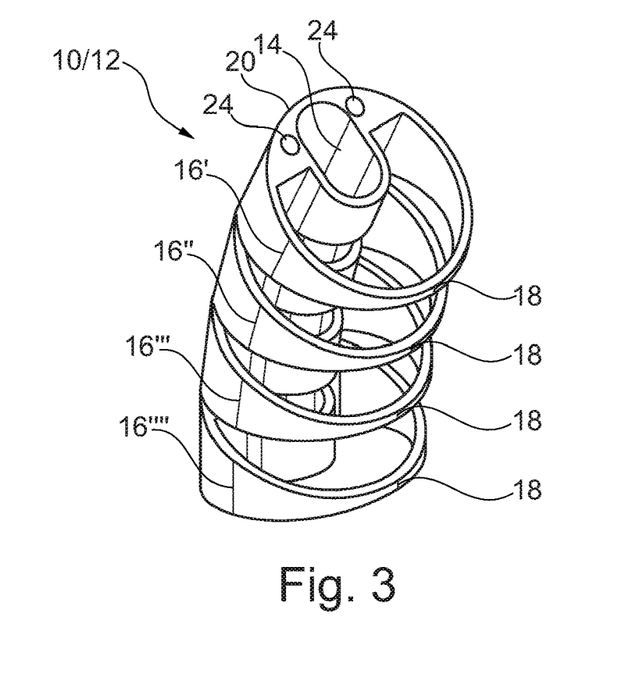
FIG. 3 is an illustration of the basic structure of the folding mechanism according to the invention in a first curved position.
Figure 4:
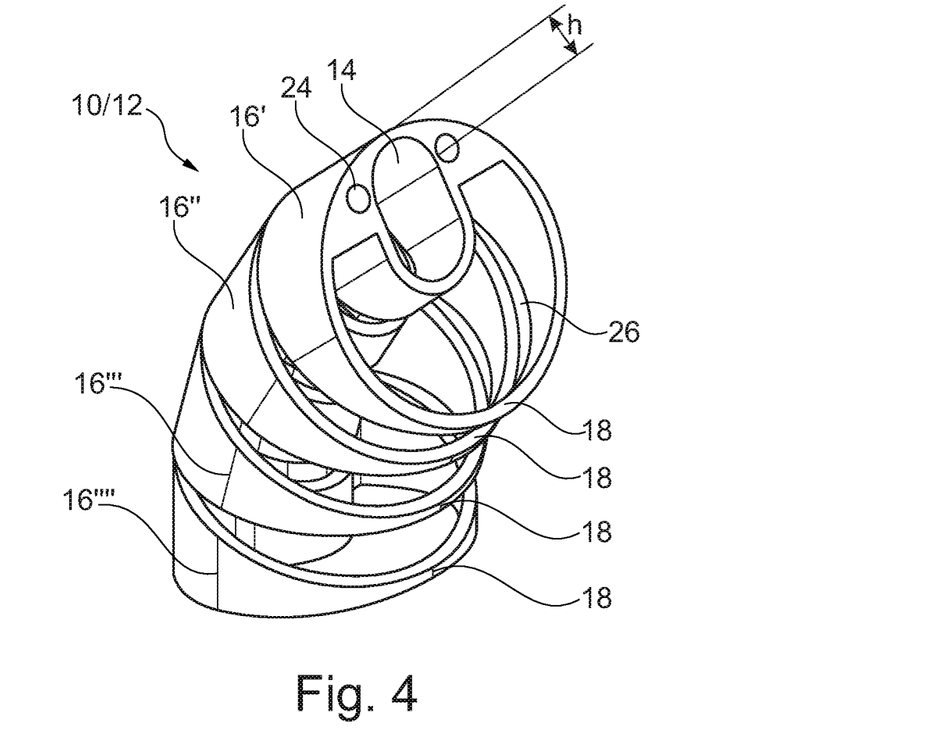
FIG. 4 is an illustration of the basic structure of the folding mechanism according to the invention in a second curved position.
Figure 5:
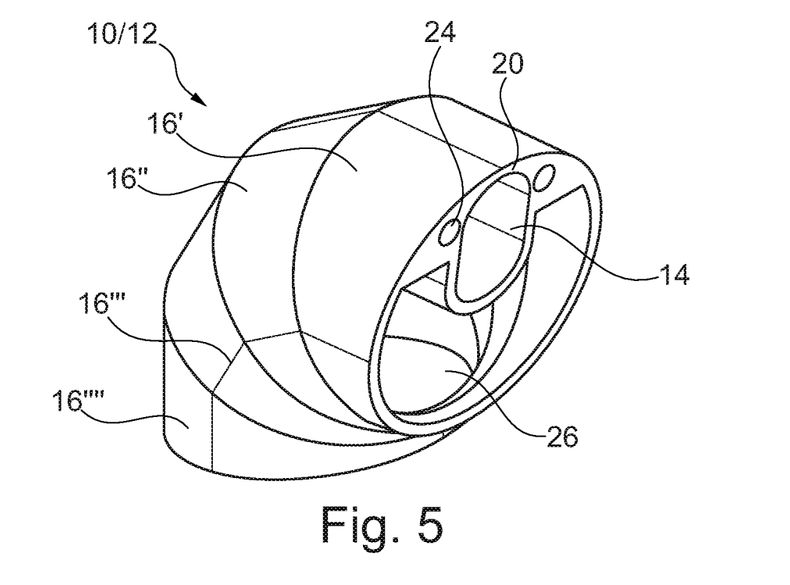
FIG. 5 is an illustration of the basic structure of the folding mechanism according to the invention in a position of maximum curvature.

In the upright configuration of the folding mechanism 10 shown in FIG. 2, the portions 20 facing away from the wedge tips 18 are adjacent to each other and form support or rest sites 22, around which the individual segments 16 can be tilted relative to each other. Due to the wedge shape of the segments 16, the base body 12 of the folding mechanism 10 has sawtooth-like clearances towards the wedge tips 18 in the upright position shown in FIG. 2. The segments 16, which can be tilted around the support or rest sites 22, can therefore be folded towards each other as shown in FIGS. 3 and 4, while reducing these clearances, until the proximal and distal front faces of adjacent segments 16 abut each other in the maximum deflected position shown in FIG. 5. Since the wedge tips have a relatively small axial extension of less than 1 mm, the 90° folded position shown in FIG. 5 can be achieved with a comparatively small inner bending radius. The advantage of the small inner bending radius is that the optical unit 6 and the lighting means 8 do not protrude far beyond the outer circumference of the endoscope in this folded position.

In the configuration example of FIGS. 2 to 5, the distal and proximal front faces of the individual segments 16 are each set at 23° to each other, resulting in a maximum folding angle of slightly more than 90° for four segments.

Figure 6:
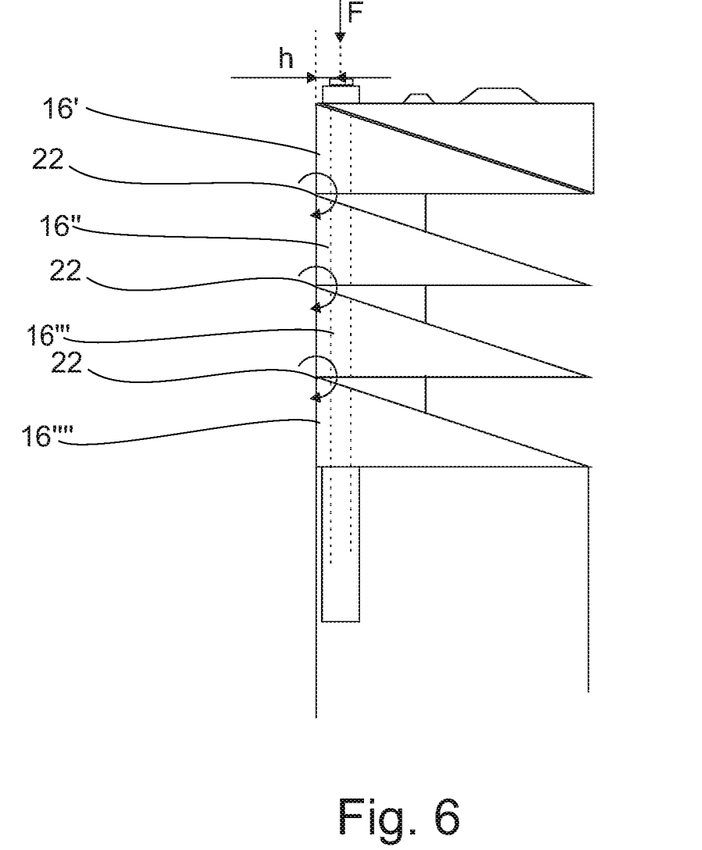
FIG. 6 is a side view of the folding mechanism according to the invention.

In order to achieve the deflection or folding described above, in the segments 16 in the area facing away from the wedge tips 18, Bowden cable channels 24 are provided, in which Bowden cables are guided, which are not shown in FIGS. 2 to 5 but which are indicated in FIG. 6. These are offset by a small distance (here: 1 to 3 mm) with respect to the support or rest sites 22 in the direction towards the wedge tips 18 so that when a traction force is applied to the most distal segment 16', a torque is generated in the support or rest sites 22 via the lever arm h (cf. FIG. 6), which is defined in this way, which causes the folding mechanism 10 to fold/deflect. Shifting the Bowden cable channels 24 to the side 10 of the segments facing away from the wedge tips 18 has the advantage that the region of the wedge tips 18 can be made thinner, which allows a smaller inner bending radius to be achieved.

In the preferred embodiment shown, the support or rest sites 22 are designed as film hinges between the segments. This has the advantage that the base body 12 can be manufactured in one piece from plastic, e.g. by injection molding. The support or rest sites 22, which are designed as articulated portions/film hinges, create a connection between the individual segments 16, so that dislocation and thus a malfunction of the folding mechanism 10 cannot occur. At the same time, the articulated portions 22, which are designed as film hinges, provide a relative pivoting of the segments 16 about a defined pivot axis.

Since the lever arm h shown in FIG. 6 is relatively short due to the design described above, relatively high traction forces may be required to fold the folding mechanism 10. This can be compensated by providing a corresponding force amplification at the operating handle of the Bowden cables, e.g. via a toggle lever or the like. As indicated in FIG.

6, the Bowden cable can be anchored to the distal front face of the most distal segment 16' and can be supported with its sleeve on the proximal segment 16''' to effectively transfer the traction force F to the folding mechanism 10.

As can be seen in FIGS. 2 to 5, the interior of each segment 16 is provided with several cavities. The successive segments each have aligned cavities, resulting in different channels in the axial direction of the folding mechanism 10.

For example, the working channel 14 runs between the two Bowden cable channels 24 in the areas 20 of the segments 16 facing away from the wedge tip 18. The reason for this is that the bending radius of the working channel 14 is kept as large as possible when the folding mechanism 10 is folded. While the smallest possible bending radius of the entire folding mechanism is desired in order to reduce the radial projection of the endoscope tip when folded, the largest possible bending radius is desired for the working channel 14 per se, so that minimally invasive surgical tools W can still be 'pushed around the curve' when the working channel 14 is folded.

The individual segments 16 further form an inner lumen 26, through which various other functional and supply channels of the endoscope 2 can be guided. Examples of these are flushing, suction and insufflation channels or electrical/electronic lines to supply the imaging unit (of an image sensor which is not shown) or the lighting means 8, which has to be led from the distal endoscope tip to a proximal base station.

The invention claimed is:

1. An endoscope comprising:
   an endoscope shaft with a distal deflection portion for bendable connection of a distal tip of the endoscope with a proximal endoscope shaft portion;
   a folding portion being formed separately from the distal deflection portion and being arranged distally of the deflection portion; and
   an endoscope head connected to the folding portion or forming the folding portion, and carrying an optical unit and lighting means that are arranged distally from the folding portion, wherein the endoscope head including the optical unit and the lighting means is foldably or bendably mounted at a distal end of the endoscope shaft via the folding portion, the folding portion comprising:
   a plurality of axially successive segments which are actively adjustable in angle relative to each other separately from a bending of the deflection section via at least one actuating element of the folding portion, the plurality of axially successive segments being configured to permit folding or bending the endoscope head including the optical unit and lighting means, and said plurality of axially successive segments defining at least one working channel in an axial direction for passage of minimally invasive surgical instruments, flushing media, or supply lines,
   the plurality of axially successive segments being wedge-shaped or wedge-like cylinder sections with front sides oriented or set against each other in a wedge-shaped manner, whereby each cylinder section forms a cylinder jacket portion with minimum axial length and a cylinder jacket portion with maximum axial length,
   wherein directly adjacent segments of the plurality of axially successive segments are oriented relative to one another in such a way that the directly adjacent segments are axially supported or rest on each other at a support or rest site at a region of their respective cylinder jacket portions of maximum axial length, whereby a hinge or joint contact is created at the support or rest site;
   wherein at least one traction element channel is provided for the at least one actuating element forming a traction element for angular adjustment of the plurality of axially successive segments, said traction element channel extending in the axial direction through each of the plurality of axially successive segments and being offset radially inwards relative to the support or rest sites of the plurality of axially successive segments, in a direction towards a wedge tip formed by the cylinder jacket portion with minimum axial length, so that the traction element running in the traction element channel forms a lever arm relative to the support or rest sites of the plurality of axially successive segments, contracting the wedge tips when a tractive force is applied; and
   wherein the at least one traction element channel is arranged in a region opposite the wedge tips in a cross-section of the plurality of axially successive segments.

2. The endoscope according to claim 1, wherein front sides of the plurality of axially successive segments comprise setting angles, said front sides extending in a wedge-shape, said plurality of axially successive segments and setting angles being matched to each other in such a way that in a maximum folded position of the folding portion, in which the directly adjacent segments abut each other, a folding angle of at least 80° is obtained.

3. The endoscope according to claim 1, wherein a wedge shape of the plurality of axially successive segments is dimensioned such that in the maximum folded position of the folding portion, an inner radius of curvature of the folding portion is less than twice a diameter of the folding portion, said diameter being defined by the plurality of axially successive segments.

4. The endoscope according to claim 1, wherein, in a 90° folded position of the folding portion, the distal front side of the endoscope head protrudes less than 2 cm beyond a lateral jacket surface of the folding portion in a prograde orientation.

5. The endoscope according to claim 1, wherein the cylinder jacket portion with minimum axial length of the plurality of axially successive segments has an axial length less than 2 mm, whereby it forms a wedge tip when viewed in a side view.

6. The endoscope according to claim 1, wherein the traction element channel comprises two traction element channels provided in respective cross-sectional regions of the plurality of axially successive segments opposite the wedge tips, between which the at least one working channel is arranged.

7. The endoscope according to claim 6, wherein the working channel has an oval cross-section whose longest diameter runs in a folding direction of the folding portion, and wherein said plurality of axially successive segments define a lumen in an axial direction for passage of one or more functional or supply channels, with the lumen at least partially surrounding the working channel.

8. The endoscope according to claim 6, wherein the two traction element channels are provided in the plurality of axially successive segments, such that one of the actuating element channels is arranged on each cross-sectional half of the plurality of axially successive segments, with a border between the plurality of axially successive segments running from portions with minimum axial length to portions with maximum axial length.

9. The endoscope according to claim 1, wherein said plurality of axially successive segments define a lumen in an axial direction for passage of one or more functional or supply channels, wherein the working channel is arranged on a laterally outer side of the folding portion in an area of an outer radius of its direction of curvature, and the lumen is arranged on a laterally inner side of the folding portion between the working channel and the cylinder jacket portion with minimum axial length of each of the plurality of axially successive segments.

10. The endoscope according to claim 1, wherein at least one of the support or rest sites between two of the directly adjacent segments is formed as a film hinge.

11. The endoscope according to claim 1, wherein the plurality of axially successive segments that are wedge-shaped are recessed in alignment in the area of their wedge tip, so that a clear region and a rib-like structure is produced towards the inner radius of curvature of the folding portion.

12. The endoscope according to claim 1, wherein the traction element comprises a cable pull.

13. An endoscope comprising:
an endoscope shaft with a distal deflection portion for bendable connection of a distal tip of the endoscope with a proximal endoscope shaft portion, the deflection portion being actively deflectable via a first actuation mechanism,
a folding portion being formed separately from the distal deflection portion and being arranged distally of the deflection portion, the folding portion being actively foldable or bendable exclusively in a two-dimensional manner via a second actuation mechanism individually and separately from the deflection portion, and
an endoscope head connected to the folding portion or forming the folding portion, and carrying an optical unit and lighting elements, wherein the endoscope head including the optical unit and the lighting elements is foldably or bendably mounted at a distal end of the deflection portion of the endoscope shaft via the folding portion, the folding portion comprising:
a plurality of axially successive segments which are actively adjustable in angle relative to each other separately from a bending of the deflection portion via at least one actuating element of the second actuation mechanism for orienting the endoscope head including the optical unit and lighting elements into a radial direction of the endoscope shaft, and said plurality of axially successive segments defining one working channel in an axial direction for passage of minimally invasive surgical instruments,
the plurality of axially successive segments being wedge-shaped or wedge-like cylinder sections with front sides oriented or set against each other in a wedge-shaped manner, whereby each cylinder section forms a cylinder jacket portion with minimum axial length and a cylinder jacket portion with maximum axial length,
wherein directly adjacent ones of the plurality of axially successive segments are oriented relative to one another in such a way that the directly adjacent segments are axially supported or rest on each other at a support or rest site at a region of their respective cylinder jacket portions of maximum axial length, whereby a hinge or joint contact is created at the support or rest site, and
wherein a respective wedge shape of each of the plurality of axially successive segments of the folding portion is dimensioned such that in a 90° folded position, the folding portion has a smaller inner radius of curvature than an inner radius of curvature of the deflection portion in a 90° deflected position, and in a maximum folded position of the folding portion, the inner radius of curvature of the folding portion is less than a single diameter of the folding portion, said diameter being defined by the plurality of axially successive segments of the folding portion, and wherein the only one working channel is located eccentric within each segment of the folding portion in a segment area close to cylinder jacket portion with maximum axial length thereby achieving a maximum possible bending radii of the working channel to allow a smooth forwarding movement of an inserted medical instrument also in a maximum bended state of the folding portion.

14. The endoscope according to claim 13, wherein, in the maximum folded position of the folding portion, the inner radius of curvature of the folding portion is less than half the diameter of the folding portion.

* * * * *